(12) United States Patent
Piron et al.

(10) Patent No.: US 9,681,821 B2
(45) Date of Patent: Jun. 20, 2017

(54) METHODS FOR MEASURING GLOBAL GLYMPHATIC FLOW USING MAGNETIC RESONANCE IMAGING

(71) Applicant: SYNAPTIVE MEDICAL (BARBADOS) INC., Bridgetown (BB)

(72) Inventors: Cameron Piron, Toronto (CA); Jeff Stainsby, Toronto (CA); Chad Harris, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 14/903,029

(22) PCT Filed: Feb. 19, 2015

(86) PCT No.: PCT/IB2015/051285
§ 371 (c)(1),
(2) Date: Feb. 3, 2016

(87) PCT Pub. No.: WO2016/132176
PCT Pub. Date: Aug. 25, 2016

(65) Prior Publication Data
US 2016/0367166 A1    Dec. 22, 2016

(51) Int. Cl.
*A61B 5/055* (2006.01)
*A61B 5/00* (2006.01)
(Continued)

(52) U.S. Cl.
CPC .............. *A61B 5/055* (2013.01); *A61B 5/031* (2013.01); *A61B 5/032* (2013.01); *A61B 5/4058* (2013.01);
(Continued)

(58) Field of Classification Search
CPC ..... A61B 2576/00; A61B 5/031; A61B 5/032; A61B 5/055; A61B 5/4058; A61B 5/4076;
(Continued)

(56) References Cited

U.S. PATENT DOCUMENTS 6,076,006 A    6/2000  Van Den Brink et al.
8,315,450 B2  11/2012  Quigley
(Continued)

FOREIGN PATENT DOCUMENTS

WO    2014130777 A1    8/2014

OTHER PUBLICATIONS

Tofts, PS et al., "Estimating Kinetic Parameters From Dynamic Contrast-Enhanced T1-Weighted MRI of Diffusable Tracer: Standardized Quantities and Symbols" Journal of MRI, vol. 10, p. 1.
(Continued)

*Primary Examiner* — Ruth S Smith
(74) *Attorney, Agent, or Firm* — Quarles & Brady, LLP

(57) ABSTRACT

Systems and methods for providing quantitative measurements of global glymphatic flow of cerebrospinal fluid ("CSF") using magnetic resonance imaging ("MRI") are described. In general, images are obtained from a subject using flow-sensitive MRI techniques that are designed to be particularly sensitive to the glymphatic flow of CSF. Measures of glymphatic flow can be obtained while the subject is in an awake state and again while the subject is in a sleep state. Based on these two measurements, a biomarker that indicates a neurological state or disease can be generated.

10 Claims, 7 Drawing Sheets

(51) Int. Cl.
*A61B 5/03* (2006.01)
*G01R 33/563* (2006.01)

(52) U.S. Cl.
CPC ...... *A61B 5/4076* (2013.01); *G01R 33/56341* (2013.01); *G01R 33/56366* (2013.01); *A61B 5/4809* (2013.01); *A61B 2576/00* (2013.01)

(58) Field of Classification Search
CPC ............ A61B 5/4809; G01R 33/56341; G01R 33/56366
See application file for complete search history.

(56) References Cited

U.S. PATENT DOCUMENTS

| | | |
|---|---|---|
| 8,903,469 B2 | 12/2014 | Yamada et al. |
| 2009/0024181 A1 | 1/2009 | Raghavan |

OTHER PUBLICATIONS

Kozak, LR et al., "Using diffusion MRI for measuring the temperature of cerebrospinal fluid within the lateral ventricles", Acta Paediatrica 2010, vol. 99, pp. 237-243.

The International Search Report and Written Opinion with a mailing date of Jul. 8, 2015 for International Application No. PCT/IB2015/051285.

METHODS FOR MEASURING GLOBAL GLYMPHATIC FLOW USING MAGNETIC RESONANCE IMAGING

CROSS-REFERENCE TO RELATED APPLICATIONS

This application represents the national stage entry of PCT International Application No. PCT/IB2015/051285 filed Feb. 19, 2015. The contents of this application are hereby incorporated by reference as if set forth in their entirety herein.

BACKGROUND OF THE INVENTION

The field of the invention is systems and methods for magnetic resonance imaging ("MRI"). More particularly, the invention relates to systems and methods for measuring global glymphatic flow in a subject using MRI.

Recent studies have indicated that the flushing of cerebral spinal fluid ("CSF") may be a mechanism that is used to eliminate toxins from the central nervous system. In general, this process is part of the so-called "glymphatic system." It would be desirable to provide systems and methods that provide a characterization or quantification of the flow of CSF through the glymphatic system because such information could provide insights into how neurological diseases develop and progress in the healthy nervous system.

For instance, it would be desirable to provide systems and methods that are capable of monitoring or otherwise characterizing a breakdown in glymphatic flow, as these changes may be caused by, or be correlated with, the pathogenesis of neurodegenerative disorders such as Alzheimer's, Parkinson's, and Huntington's disease, in addition to amyotropic lateral sclerosis ("ALS") and chronic traumatic encephalopathy.

Recently, researchers have investigated whether glymphatic flow can be imaged using MRI. For instance, contrast-enhanced MRI techniques were used to map regions of high and low volume solute exchange. While these studies were able to provide qualitative information about relative glymphatic flow, it would be more desirable to provide systems and methods that are capable of providing quantitative measures of glymphatic flow.

SUMMARY OF THE INVENTION

The present invention overcomes the aforementioned drawbacks by providing a method for measuring glymphatic flow in a subject using magnetic resonance imaging ("MRI"). In general, the method includes directing the MRI system to acquire data from a subject using a pulse sequence that induces an image contrast in the acquired data that is associated with glymphatic flow. At least one image is reconstructed from the acquired data and a measure of global glymphatic flow is estimated based on, or from, the at least one reconstructed image.

It is an aspect of the invention that data can be acquired following the administration of a contrast agent to the subject's cerebrospinal fluid ("CSF"), where the data can be acquired while the contrast agent is perfusing through the subject's tissues or flowing through the subject's central nervous system.

It is another aspect of the invention that data can be acquired as control data and spin-labeled data. Spin-labeled data can be acquired from an imaging region in the subject by applying a radio frequency ("RF") pulse to a labeling region in the subject that is proximal to the imaging region, such that spins associated with cerebrospinal fluid are labeled and flow into the imaging region while the spin-labeled data is acquired. Control data can be acquired from the imaging region in the subject, wherein an RF pulse is not applied to the labeling region prior to acquiring the control data from the imaging region.

It is another aspect of the invention that data can be acquired using a phase contrast pulse sequence that is configured to impart a phase contrast to cerebrospinal fluid flowing though the subject's central nervous system.

It is another aspect of the invention that data can be acquired as diffusion-weighted data using a pulse sequence that includes diffusion-encoding gradients that are designed to have a b-value sufficient to sensitize the diffusion-weighted data to at least one of perfusion of CSF and bulk flow of CSF.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
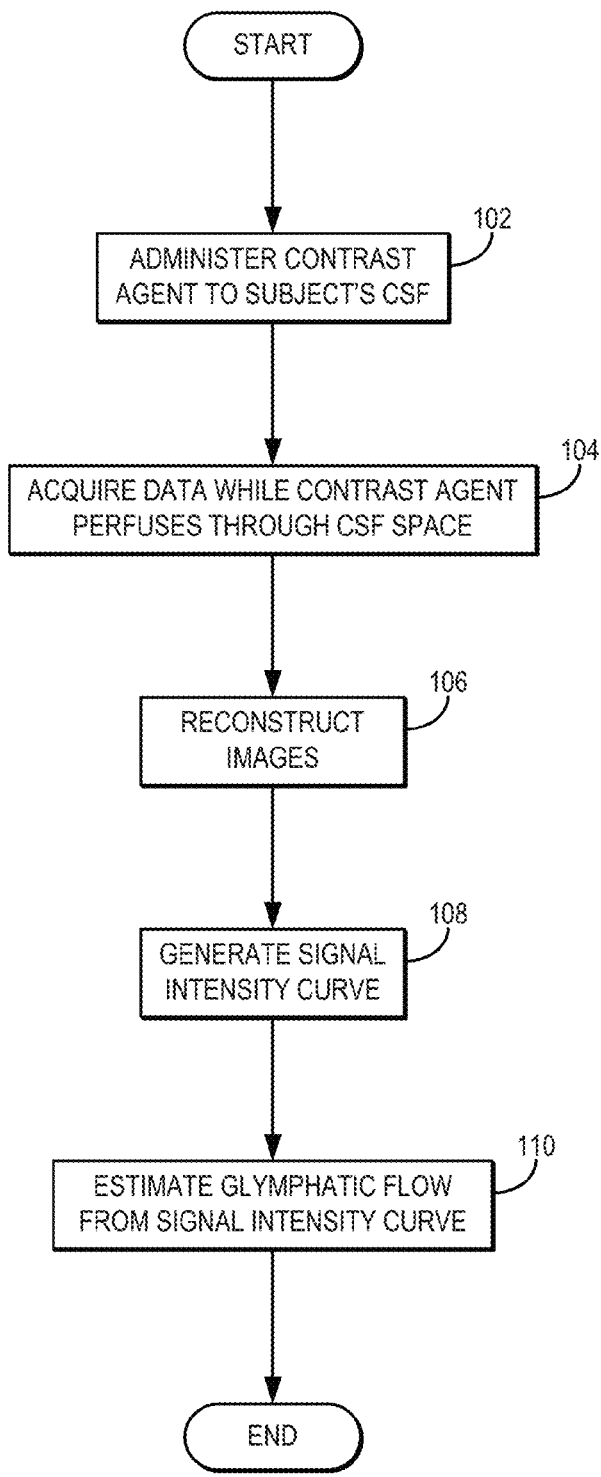
FIG. 1 is a flowchart setting forth the steps of an example of a method for measuring glymphatic flow based on contrast-enhanced cerebrospinal fluid ("CSF") perfusion imaging.

Described here are systems and methods for providing quantitative measurements of global cerebrospinal fluid ("CSF") flow using magnetic resonance imaging ("MRI"). In general, images are obtained from a subject using flow-sensitive MRI techniques that are designed to be particularly sensitive to the flow of CSF.

Based on these measurements, glymphatic flow can be characterized. Glymphatic flow generally refers to the flow of CSF through the body's glymphatic system, which is a functional waste clearance pathway for the central nervous system ("CNS"). The glymphatic system is responsible for removing interstitial fluid and extracellular fluid during a sleeping state. These two measurements can then be correlated to a metric that indicates neurological pathology. The measurements of glymphatic flow provided by the present invention are thus capable of generating imaging biomarkers for assessing neurological pathologies.

The systems and methods described here provide flow-sensitive imaging techniques that are specifically designed to measure glymphatic flow in the central nervous system (e.g., the brain and spine) of a subject, and to quantify this glymphatic flow both in awake and asleep subjects. In general, because the glymphatic flow is a "flushing" of the brain by CSF, the systems and methods described here that can be used to measure and quantify glymphatic flow can be designed to target bulk CSF flow and/or tissue-level CSF flow (i.e., CSF perfusion), as will be described below in detail.

When quantifying glymphatic flow during a sleep state, it may be preferable to monitor the subject to identify when the subject is in a particular state of sleep or rest. To this end, data acquisition with the MRI system can be triggered by, or otherwise synchronized with, data that indicates the subject's particular sleep or rest state. As one example, this data can be provided using electroencephalography ("EEG"). As another example, this data can be provided by monitoring the subject, such as by video monitoring of the subject.

Contrast-Enhanced CSF Perfusion Imaging

In some embodiments, glymphatic flow can be measured using a pulse sequence that is designed to acquire data that is sensitive to tissue-level CSF flow. As one particular example, a conventional perfusion MRI technique can be specifically adapted to measure tissue-level CSF flow through the glymphatic system.

In conventional perfusion MRI techniques, a contrast agent is injected into the subject's blood stream, and perfusion metrics are estimated from data acquisitions that are sensitive to the contrast agent, such as $T^*_2$-weighted or $T_1$-weighted imaging. For instance, the subject's blood volume can be estimated because, in healthy brain tissues, the blood brain barrier keeps the contrast agent in the intravascular space.

As one example, glymphatic flow can also be measured using tissue-level perfusion with contrast-enhanced MRI. In these embodiments, a contrast agent can be administered to a subject's CSF, such as by injecting the contrast agent into the subject's CSF. Contrast agent-sensitive MR imaging can then be performed at a timescale consistent with CSF flow. Models of perfusion contrast kinetics can then be applied to the acquired images to estimate a measure of glymphatic flow. These embodiments would be advantageous for CSF perfusion and glymphatic flow at the brain tissue level.

Thus, in these embodiments, a contrast agent is administered to the subject and a series of MR images are acquired as the contrast agent perfuses into the tissues-of-interest. Examples of contrast agents include intravenous gadolinium-based contrast agents, superparamagnetic iron oxide ("SPIO")-based contrast agents, and other nanoparticle-based contrast agents that can naturally perfuse through the brain, including small molecule agents or nano-bubbles of oxygenation. From the acquired series of contrast-enhanced MR images, a measurement of glymphatic flow can be computed.

It is possible to assess glymphatic flow by analyzing MR signal intensity changes after the first pass of the contrast agent. While passing through the interstitial space, a short bolus of contrast agent produces local magnetic field inhomogeneities that lead to a reduction in the transverse magnetization relaxation time of the bulk tissue. This susceptibility effect can be recorded by a series of rapidly acquired $T^*_2$-weighted images that reveal how the MR signal changes during the first pass of the contrast agent. The resulting MR signal intensity versus time curves can be converted into contrast agent concentration-time curves. Measures of glymphatic flow can then be derived or otherwise determined from these curves.

Referring now to FIG. 1, a flowchart is illustrated as setting forth the steps of an example method for measuring glymphatic flow from tissue-level measurements of CSF perfusion. The method begins with the administration of a contrast agent to the subject, as indicated at step 102. For instance, the contrast agent can be administered to the subject's CSF space. Data is then acquired as the contrast agent perfuses through the subject's tissues, as indicated at step 104. As one example, this data can be acquired using a $T^*_2$-weighted pulse sequence using a data acquisition that is performed on a timescale that is consistent with CSF flow rather than blood flow.

A series of images are then reconstructed from the acquired data, as indicated at step 106. From these images, a time-varying signal intensity curve associated with the CSF-mediated perfusion of the contrast agent is generated, as indicated at step 108. A measurement of glymphatic flow can then be estimated from this signal intensity curve, as indicated at step 110. As one example, the glymphatic flow can be quantified using a model of perfusion contrast kinetics.

In some embodiments, this method can be repeated twice: once while the subject is in an awake state and once while the subject is in a sleep, or other rest, state. The measurements of glymphatic flow that are obtained for these two different states can then be compared to assess the neurological function or state of the subject. In some other embodiments, rather than compare absolute measurements of glymphatic flow in an awake state and a sleep state, the relative change—whether an increase or a decrease—in glymphatic flow between the two states can be measured. For instance, images corresponding to the awake state and images corresponding to the sleep state can be reconstructed and used to estimate a measure of the relative change in glymphatic flow between the two states, rather than estimating the absolute flow for the two states separately.

In both of these example, the absolute measures of the glymphatic flow, or the relative change in flow between the two states, can be used as a biomarker that characterizes or otherwise indicates neurological function or disease. For instance, quantifying, or otherwise characterizing, changes in glymphatic flow can be used to assist in the evaluation of a neurological state of a subject. As one example, poor glymphatic flow can implicate the presence of white matter diseases; thus, the measure of glymphatic flow, or changes in glymphatic flow between awake and sleep states, can be useful as a biomarker implicating neurological disease.

Preferably, quiet MRI techniques can be used when measuring glymphatic flow during a sleep, or other rest, state. In general, quiet MRI techniques involve applying pulse sequence designs in which the rate of change of the magnetic gradients used for imaging is low throughout the entire scan. As a result of this slow rate of change, the acoustic noise created by the MRI scanner is minimized. Quiet MRI techniques can also be achieved through hardware design of the MRI system. As one example, the gradient system can be designed to minimize vibration forces generated by the gradient coils, or the MRI system can generally designed to dampen acoustic transmission in the system. Applying such quiet MRI techniques to glymphatic flow characterization would enable measurement of glymphatic flow in subjects that are in a sleep state.

Contrast-Enhanced CSF Flow Imaging

In some other embodiments, the larger CSF flow volumes can be imaged, from which a measurement of bulk glymphatic flow can be estimated. As one example, the larger CSF volumes can be dynamically imaged over time following an administration of a contrast agent into the CSF space. Based on images acquired in this manner, the rate of enhancement within the CSF space can be directly monitored. From this rate of enhancement the relative flow rate within the CSF can be calculated. Thus, a measure of glymphatic flow can be estimated.

Figure 2:
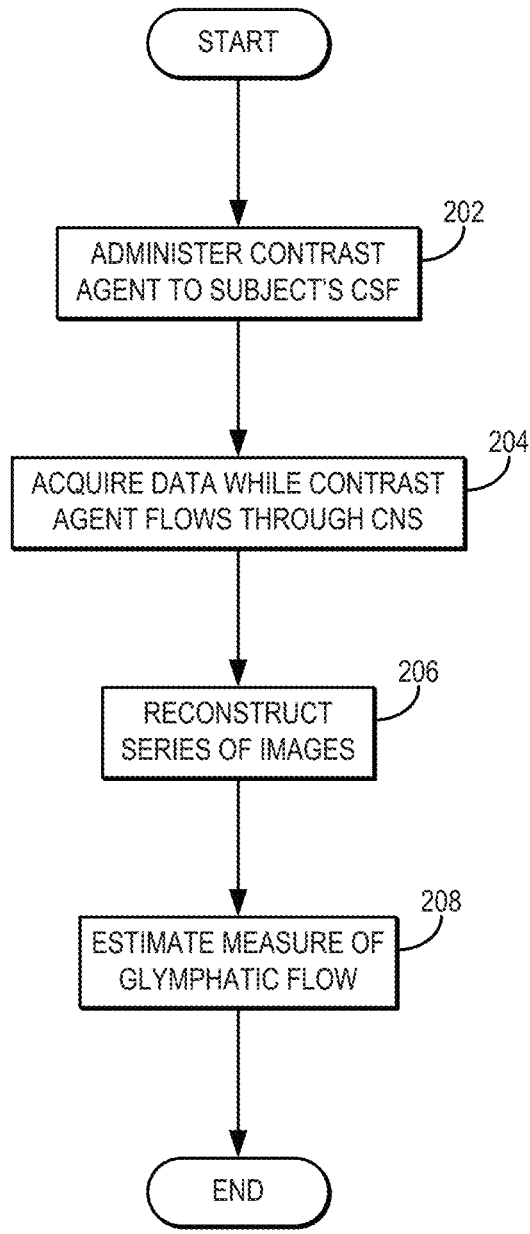
FIG. 2 is a flowchart setting forth the steps of an example of a method for measuring glymphatic flow based on contrast-enhanced bulk CSF flow imaging.

Referring now to FIG. 2, a flowchart is illustrated as setting forth the steps of an example method for measuring glymphatic flow from images of bulk CSF flow. The method begins with the administration of a contrast agent to the subject, as indicated at step 202. For instance, the contrast agent can be administered to the subject's CSF space. Data is then acquired as the contrast agent flows through the subject's central nervous system, as indicated at step 204. As one example, this data can be acquired using a any suitable pulse sequence using a data acquisition that is performed on a timescale that is consistent with CSF flow rather than blood flow.

A series of images are then reconstructed from the acquired data, as indicated at step 206. From these images, a measurement of glymphatic flow can then be estimated, as indicated at step 208.

In some embodiments, this method can be repeated twice: once while the subject is in an awake state and once while the subject is in a sleep, or other rest, state. The measurements of glymphatic flow that are obtained for these two different states can then be compared to assess the neurological function or state of the subject. As described above, quiet MRI techniques can be applied when acquiring data from a subject during a sleep, or other rest, state.

Spin-Labeled CSF Perfusion Imaging

The aforementioned methods for quantifying glymphatic flow are based on contrast-enhanced imaging techniques. In many instances, however, it may be advantageous to use a non-contrast-enhanced imaging technique to assess glymphatic flow. As one example, subjects who have impaired kidney function may develop nephrogenic systemic fibrosis ("NSF") as a result of exposure to gadolinium-based contrast agents. For these subjects, non-contrast-enhanced methods will be preferred.

Thus, glymphatic flow can also be measured based on images acquired using non-contrast-enhanced techniques that are specifically designed to be sensitive to glymphatic flow.

In some embodiments, glymphatic flow can be measured from images that are acquired using a pulse sequence that tags, or otherwise labels, spins associated with CSF that are inflowing into a target imaging region, which may be an imaging slice or an imaging volume.

Figure 3:
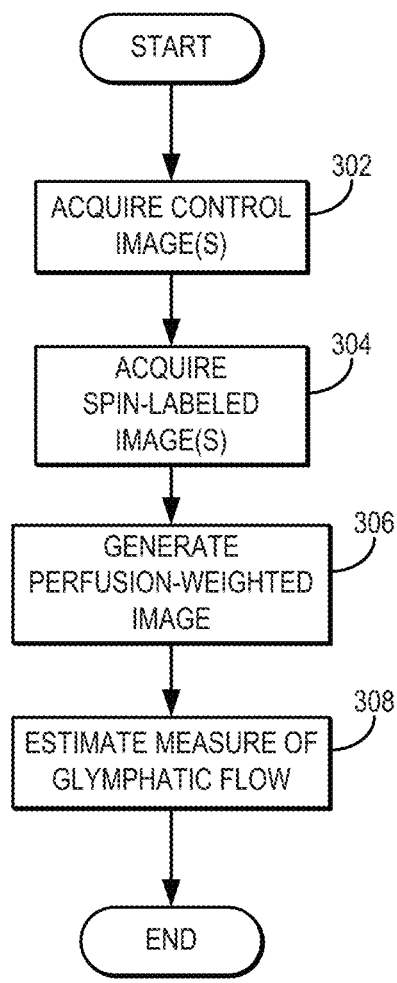
FIG. 3 is a flowchart setting forth the steps of an example of a method for measuring glymphatic flow based on spin-labeled, or spin-tagged, imaging techniques.

Referring now to FIG. 3, a flowchart is illustrated as setting forth the steps of an example method for measuring glymphatic flow based on images acquired using a spin labeling pulse sequence. The method begins with the acquisition of a control image that is acquired without labeling the CSF spins, as indicated at step 302. A spin-labeled image is then acquired, as generally indicated at step 304.

The acquisition of the spin-labeled image generally includes using a pulse sequence that labels CSF spins that are flowing into a target imaging region. As one example, the CSF spins can be labeled by applying an inversion or saturation radio frequency ("RF") pulse proximal to the target imaging region. In this manner, the CSF spins are magnetically labeled some distance away from the imaging slice or volume. As the labeled CSF flows into the imaging region the inflow is detected as a modulation of the longitudinal magnetization.

The successfulness of implementing this spin-labeling technique depends on accurately determining when the tagged CSF enters and leaves the imaging region because ill-timed image acquisitions can result in signal loss or artifacts in the reconstructed image. Thus, the timing of the spin-labeling RF pulse and the data acquisition can be determined based on the timescale of glymphatic flow.

In some embodiments, a time-resolved perfusion imaging technique can be implemented to help evaluate perfusion evolution dynamics. Using a time-resolved imaging technique also has the benefit of reducing the sensitivity of the imaging technique to exact prescription of timing parameters. For instance, a time-resolved method can be used to acquire multiple imaging volumes, each representing the location of the tagged CSF at a different delay time relative to the application of the spin-labeling RF pulse.

In some examples, an imaging protocol can be established in which areas having low-flow are locally tagged to identify regions that may have flow issues. Regions that are identified as such can then be systematically imaged and evaluated.

In general, CSF has a significantly longer $T_1$ relaxation time than surrounding tissues, and also takes a relatively long time to perfuse into the brain. As a result, the acquisition of the spin-labeled image should include parameters that are specific to the CSF $T_1$ relaxation time and expected perfusion rates. For instance, because CSF travels slower than blood, the spin-labeled volume should be selected to be close to the imaging volume. This allows tagged blood to flow out of the imaging volume while keeping the tagged CSF in the imaging volume during data acquisition.

A perfusion-weighted image can then be generated by subtracting the control image and the spin-labeled image, as indicated at step 306. Based on this perfusion-weighted image, glymphatic flow can be measured or otherwise quantified, as indicated at step 308.

In some embodiments, this method can be repeated twice: once while the subject is in an awake state and once while the subject is in a sleep, or other rest, state. The measurements of glymphatic flow that are obtained for these two different states can then be compared to assess the neurological function or state of the subject. As described above, quiet MRI techniques can be applied when acquiring data from a subject during a sleep, or other rest, state.

Phase-Contrast CSF Flow Imaging

Another example of a non-contrast-enhanced imaging technique that can be adapted to measure glymphatic flow includes phase contrast imaging techniques. Thus, in some embodiments, phase contrast imaging can be used to acquire images, from which glymphatic flow can be measured.

In general, phase contrast imaging techniques encode spin motion into the phase of the acquired signal. These imaging techniques derive contrast between flowing spins and stationary tissues by manipulating the phase of the magnetization, such that the phase of the magnetization from the stationary spins is zero and the phase of the magnetization from the moving spins is non-zero.

As one example, motion encoding gradients that are sensitive to velocity components in two or three orthogonal directions can be used. In this acquisition technique, spins that are moving along the direction of the motion encoding gradient will receive a phase shift that is proportional to their velocity. From the resulting velocity component images, total quantitative flow images can be produced, from which glymphatic flow can be quantified.

Phase contrast acquisitions are thus designed so that specific flow rates will result in specific signal phases in the phase difference data. This imaging technique can, therefore, be suitably adapted to image bulk CSF flow in the larger CSF volumes. Moreover, phase contrast imaging techniques can be adapted to measure bulk CSF flow at different, times or in different states, such as during a rest state or an awake state.

Figure 4:
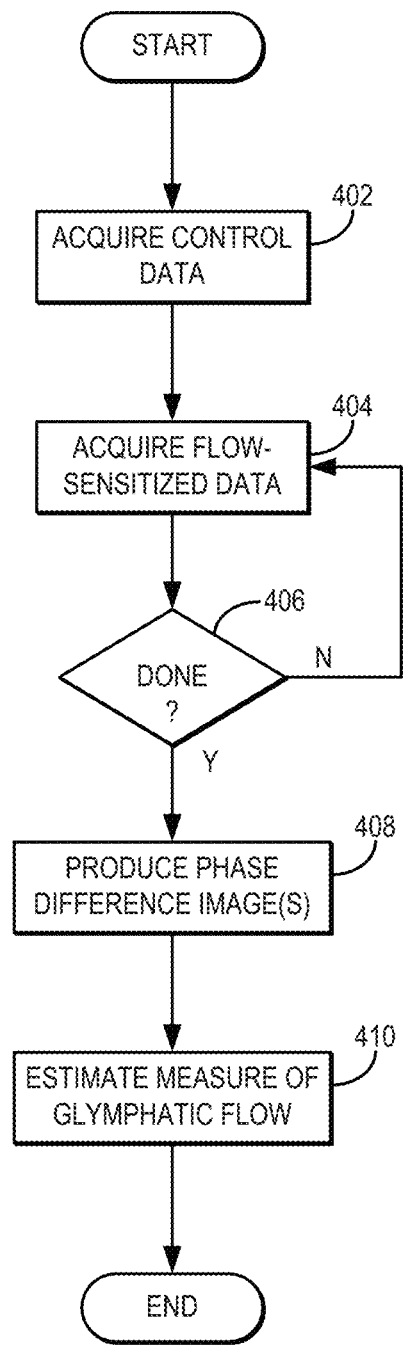
FIG. 4 is a flowchart setting forth the steps of an example of a method for measuring glymphatic flow based on phase contrast imaging techniques.

Referring now to FIG. 4, a flowchart is illustrated as setting forth the steps of an example method for measuring glymphatic flow based on a phase contrast imaging technique. The method begins with the acquisition of control data, in which no motion encoding gradients are applied, as indicated at step 402. Next, flow-sensitized data is acquired using a pulse sequence in which motion encoding gradients are applied, as indicated at step 404. In this acquisition, stationary tissues will not experience a phase change from the motion encoding gradients, but spins moving along the direction of the motion encoding gradients will experience a phase shift. As indicated at decision block 406, if motion encoding along additional directions is desired, step 404 can be repeated while changing the direction of the motion encoding gradients for each repetition. Step 404 can also be repeated to acquire data that is sensitive to different flow rates by suitably changing the motion encoding gradients to be sensitive to different flow rates, such as by changing a user-selected velocity-encoding ("VENC") value.

After the control data and the desired amount of flow-sensitized data have been acquired, one or more phase difference images are produced, as indicated at step 408. Each phase difference, or phase contrast, image can be generated by first computing phase difference data by subtracting one set of flow-sensitized data and the control data. From the phase difference data, a phase difference, or phase contrast, image can then be reconstructed. The phase difference data can be computed using a phase difference or complex difference technique, as is known in the art.

From the one or more phase contrast images, a measure of glymphatic flow can be estimated, as indicated at step 410. In some embodiments, this method can be repeated twice: once while the subject is in an awake state and once while the subject is in a sleep, or other rest, state. The measurements of glymphatic flow that are obtained for these two different states can then be compared to assess the neurological function or state of the subject. As described above, quiet MRI techniques can be applied when acquiring data from a subject during a sleep, or other rest, state.

Diffusion-Sensitive CSF Flow Imaging

Still other embodiments for acquiring magnetic resonance images from which glymphatic flow can be estimated include methods based on diffusion imaging principles.

Figure 5:
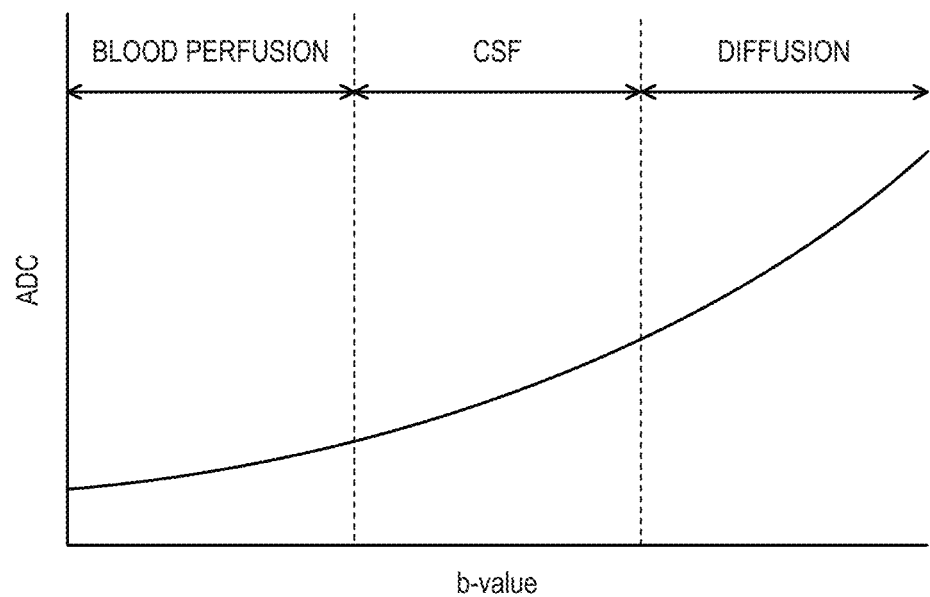
FIG. 5 is a plot illustrating a range of b-values that is correlated with CSF perfusion and bulk flow rates rather than blood perfusion and flow or cellular diffusion.

In general, diffusion MRI is a technique that sensitizes the magnetic resonance signal to the amount of random water movement. It is contemplated that CSF perfusion rates and bulk CSF flow rates would fall between blood flow rates and tissue water diffusion rates. As a result, diffusion imaging techniques can be particularly tailored to generate an image contrast that differentiates glymphatic flow related to CSF perfusion and bulk flow. For example, as illustrated in FIG. 5, a diffusion imaging pulse sequence can be designed such that the b-value defined by the diffusion gradients and their timing will result in spins associated with CSF perfusion and bulk flow to be selectively sensitized.

Quantitative diffusion measurements with diffusion encoding applied at a level that would be most sensitive to water motion associated with these CSF perfusion and bulk flow rates can therefore provide for the characterization and quantification of glymphatic flow. Furthermore, directional diffusion measurements (e.g., those obtained using diffusion tenor imaging) may provide additional directional information about the glymphatic flow.

Figure 6:
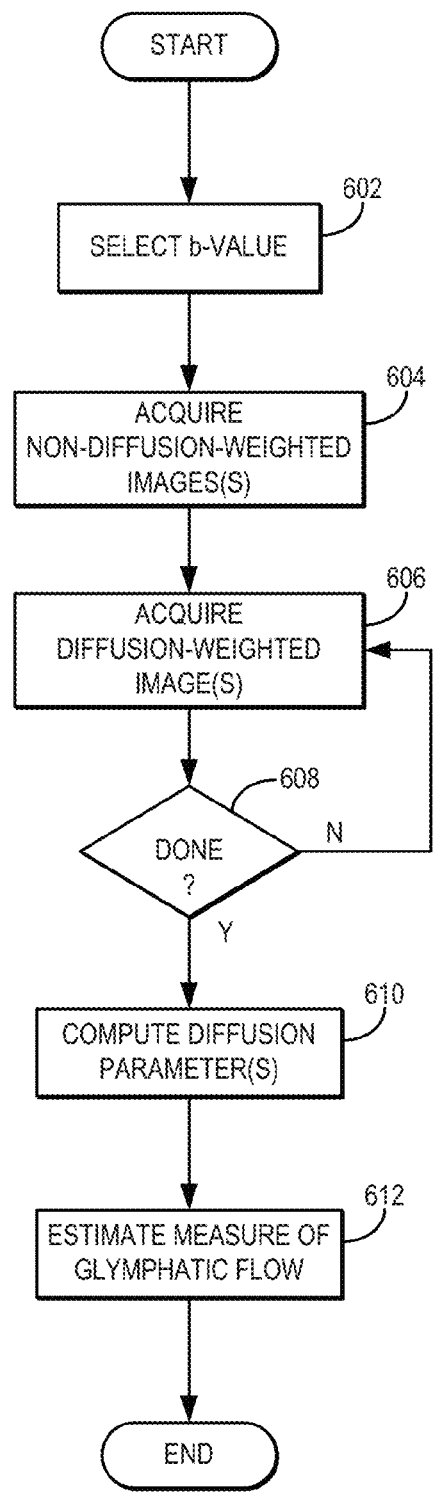
FIG. 6 is a flowchart setting forth the steps of an example of a method for measuring glymphatic flow based on diffusion-weighted imaging ("DWI") techniques, including diffusion tensor imaging ("DTI")

Referring now to FIG. 6, a flowchart is illustrated as setting forth the steps of an example method for measuring glymphatic flow based on a diffusion imaging technique. The method begins by selecting a b-value, or otherwise designing diffusion gradients, that will result in sensitizing flow specific to CSF perfusion and bulk flow rates, as indicated at step 602. As one example, the b-value can be selected in a range of about 100 $s^2$/mm to about 1000 $s^2$/mm. In some embodiments, multiple different b-values can be selected across a range of values.

Non-diffusion-weighted images are acquired, as indicated at step 604. Preferably, the non-diffusion-weighted images are acquired using the same pulse sequence that will be used to acquire diffusion-weighted images, but with the b-value set to zero (i.e., without diffusion encoding gradients). Diffusion-weighted images are then acquired using a pulse sequence that includes diffusion-encoding gradients that are designed according to the selected b-value, as indicated at step 606. In some embodiments, blood signals can be saturated before acquiring the non-diffusion-weighted data, the diffusion-weighted data, or both, thereby improving the acquired CSF signal.

In some other embodiments, multiple sets of diffusion-weighted images can be acquired by using a different b-value for each set of images. As one example, different image sets can be acquired using b-values over a range of relatively small b-values (e.g., 0 $s^2$/mm to about 100 $s^2$/mm) to characterize "fast" moving water. If signals from blood have been saturated, as described above, then it is contemplated that the contribution of perfusion effects to the diffusion curve will be indicative of CSF flow rather than blood flow. Because the CSF flow should be slower than blood flow, a larger range of relatively small b-values can be used to gather information about this effect.

If directional information is desired, as determined at decision block 608, additional diffusion-weighted images can be acquired by repeating step 606 while changing the diffusion-encoding direction defined by the diffusion-encoding gradients. When the desired amount of images has been acquired, diffusion parameters are computed, as indicated at step 610. As one example, the diffusion parameter can include the apparent diffusion coefficient ("ADC"). As another example, the diffusion parameter can include those computed from a diffusion tensor, including mean diffusivity and fractional anisotropy.

The computed diffusion parameters can then be used to estimate or otherwise characterize the glymphatic flow, as indicated at step 612. In some embodiments, this method can be repeated twice: once while the subject is in an awake state and once while the subject is in a sleep, or other rest, state. The measurements of glymphatic flow that are obtained for these two different states can then be compared to assess the neurological function or state of the subject. As described above, quiet MRI techniques can be applied when acquiring data from a subject during a sleep, or other rest, state.

Spatially-Selective Measurements

Many of the aforementioned data acquisition techniques can be augmented using a spatially-selective excitation, such as by using an RF excitation profile that is focused to excite only a small volume. As one example, the small volume can include a cylindrical volume that encompasses a region where CSF resides within the CNS at a given time. For instance, a small cylindrical volume within the brainstem can be selectively excited.

Advantageously, using a spatially-selective excitation a high-temporal resolution data set can be acquired, from which an estimate of how long it takes for the excited, or otherwise labeled, signal to travel to a desired imaging region. Based on this information, a flow rate for the CSF can be determined. One example of a high-temporal resolution acquisition that can be used in these instances includes a magic angle radial acquisition scheme. This procedure can be repeated over a long period of time to track changes in CSF flow and, therefore, in glymphatic flow.

The methods for quantifying glymphatic flow described here can be used to map the volume of the interstitial space in the subject's brain and how it varies over the sleep pattern of the subject. It is contemplated that a long term measurement of changes in how the volume of the interstitial space varies over the sleep pattern of the subject can be used as a precursor to different neurological diseases.

Figure 7:
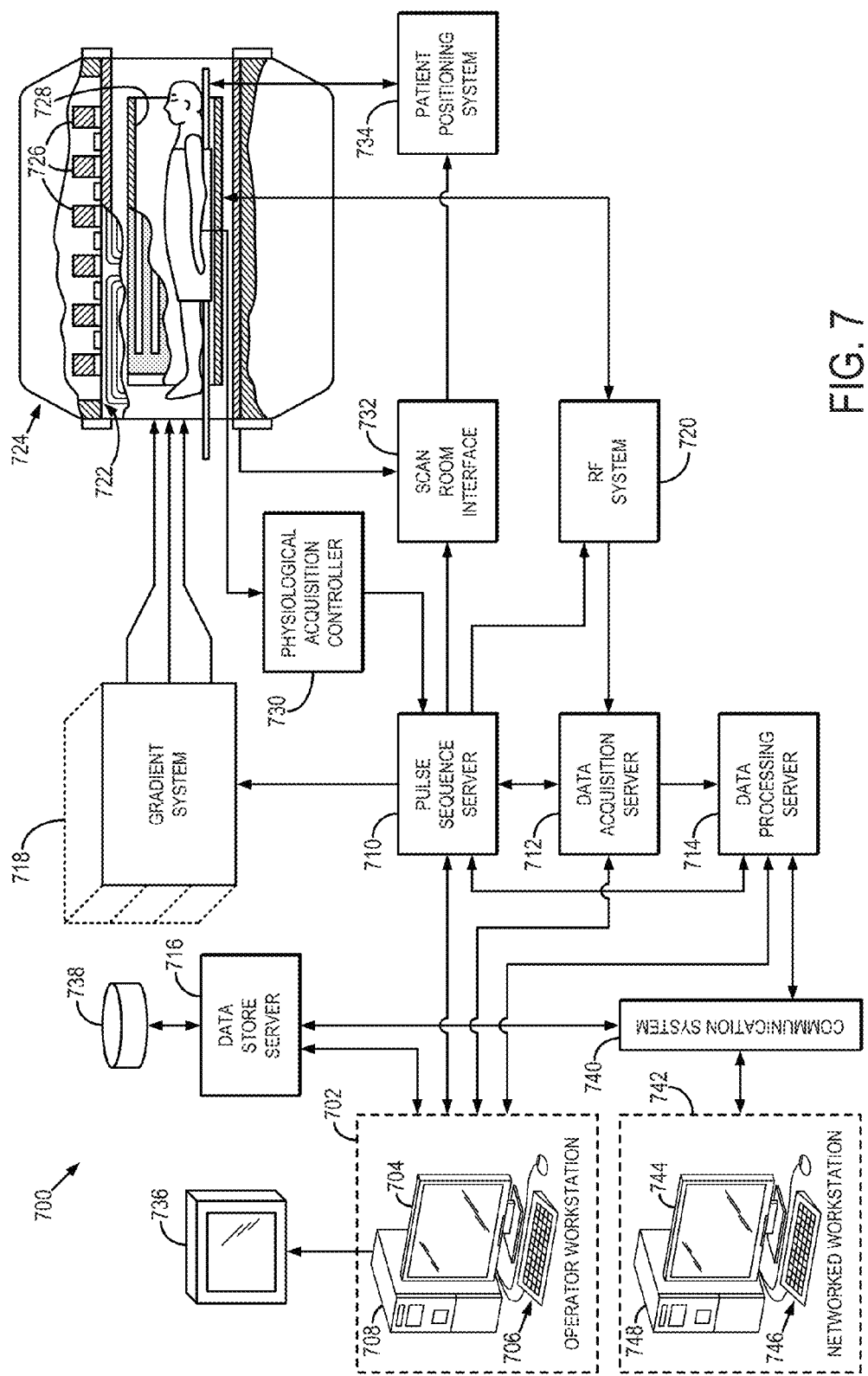
FIG. 7 is a block diagram of an example of a magnetic resonance imaging ("MRI") system.

Referring particularly now to FIG. 7, an example of a magnetic resonance imaging ("MRI") system 700 is illustrated. The MRI system 700 includes an operator workstation 702, which will typically include a display 704; one or more input devices 706, such as a keyboard and mouse; and a processor 708. The processor 708 may include a commercially available programmable machine running a commercially available operating system. The operator workstation 702 provides the operator interface that enables scan prescriptions to be entered into the MRI system 700. In general, the operator workstation 702 may be coupled to four servers: a pulse sequence server 710; a data acquisition server 712; a data processing server 714; and a data store server 716. The operator workstation 702 and each server 710, 712, 714, and 716 are connected to communicate with each other. For example, the servers 710, 712, 714, and 716 may be connected via a communication system 740, which may include any suitable network connection, whether wired, wireless, or a combination of both. As an example, the communication system 740 may include both proprietary or dedicated networks, as well as open networks, such as the internet.

The pulse sequence server 710 functions in response to instructions downloaded from the operator workstation 702 to operate a gradient system 718 and a radiofrequency ("RF") system 720. Gradient waveforms necessary to perform the prescribed scan are produced and applied to the gradient system 718, which excites gradient coils in an assembly 722 to produce the magnetic field gradients $G_x$, $G_y$, and $G_z$ used for position encoding magnetic resonance signals. The gradient coil assembly 722 forms part of a magnet assembly 724 that includes a polarizing magnet 726 and a whole-body RF coil 728. In some embodiments, the gradient system 718 is preferably capable of achieving high gradient power. In some other embodiments, the gradient system 718 is capable of operating in a quiet MRI mode, such as by slowly varying the magnetic field gradients to minimize acoustic noise generated by the gradient coil assembly 722 during imaging.

RF waveforms are applied by the RF system 720 to the RF coil 728, or a separate local coil (not shown FIG. 7), in order to perform the prescribed magnetic resonance pulse sequence. Responsive magnetic resonance signals detected by the RF coil 728, or a separate local coil (not shown in FIG. 7), are received by the RF system 720, where they are amplified, demodulated, filtered, and digitized under direction of commands produced by the pulse sequence server 710. The RF system 720 includes an RF transmitter for producing a wide variety of RF pulses used in MRI pulse sequences. The RF transmitter is responsive to the scan prescription and direction from the pulse sequence server 710 to produce RF pulses of the desired frequency, phase, and pulse amplitude waveform. The generated RF pulses may be applied to the whole-body RF coil 728 or to one or more local coils or coil arrays (not shown in FIG. 7).

The RF system 720 also includes one or more RF receiver channels. Each RF receiver channel includes an RF preamplifier that amplifies the magnetic resonance signal received by the coil 728 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \qquad (1);$$

and the phase of the received magnetic resonance signal may also be determined according to the following relationship:

$$\varphi = \tan^{-1}\left(\frac{Q}{I}\right). \qquad (2)$$

The pulse sequence server 710 also optionally receives patient data from a physiological acquisition controller 730. By way of example, the physiological acquisition controller 730 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 710 to synchronize, or "gate," the performance of the scan with the subject's heart beat or respiration.

The pulse sequence server 710 also connects to a scan room interface circuit 732 that receives signals from various sensors associated with the condition of the patient and the magnet system. It is also through the scan room interface circuit 732 that a patient positioning system 734 receives commands to move the patient to desired positions during the scan.

The digitized magnetic resonance signal samples produced by the RF system 720 are received by the data acquisition server 712. The data acquisition server 712 operates in response to instructions downloaded from the operator workstation 702 to receive the real-time magnetic resonance data and provide buffer storage, such that no data is lost by data overrun. In some scans, the data acquisition server 712 does little more than pass the acquired magnetic resonance data to the data processor server 714. However, in scans that require information derived from acquired magnetic resonance data to control the further performance of the scan, the data acquisition server 712 is programmed to produce such information and convey it to the pulse sequence server 710. For example, during prescans, magnetic resonance data is acquired and used to calibrate the pulse sequence performed by the pulse sequence server 710. As another example, navigator signals may be acquired and used to adjust the operating parameters of the RF system 720 or the gradient system 718, or to control the view order in which k-space is sampled. In still another example, the data acquisition server 712 may also be employed to process magnetic resonance signals used to detect the arrival of a contrast agent in a magnetic resonance angiography ("MRA") scan. By way of example, the data acquisition server 712 acquires magnetic resonance data and processes it in real-time to produce information that is used to control the scan.

The data processing server 714 receives magnetic resonance data from the data acquisition server 712 and processes it in accordance with instructions downloaded from the operator workstation 702. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 714 are conveyed back to the operator workstation 702 where they are stored. Real-time images are stored in a data base memory cache (not shown in FIG. 7), from which they may be output to operator display 712 or a display 736 that is located near the magnet assembly 724 for use by attending physicians. Batch mode images or selected real time images are stored in a host database on disc storage 738. When such images have been reconstructed and transferred to storage, the data processing server 714 notifies the data store server 716 on the operator workstation 702. The operator workstation 702 may be used by an operator to archive the images, produce films, or send the images via a network to other facilities.

The MRI system 700 may also include one or more networked workstations 742. By way of example, a networked workstation 742 may include a display 744; one or more input devices 746, such as a keyboard and mouse; and a processor 748. The networked workstation 742 may be located within the same facility as the operator workstation 702, or in a different facility, such as a different healthcare institution or clinic.

The networked workstation 742, whether within the same facility or in a different facility as the operator workstation 702, may gain remote access to the data processing server 714 or data store server 716 via the communication system 740. Accordingly, multiple networked workstations 742 may have access to the data processing server 714 and the data store server 716. In this manner, magnetic resonance data, reconstructed images, or other data may be exchanged between the data processing server 714 or the data store server 716 and the networked workstations 742, such that the data or images may be remotely processed by a networked workstation 742. This data may be exchanged in any suitable format, such as in accordance with the transmission control protocol ("TCP"), the internet protocol ("IP"), or other known or suitable protocols.

The present invention has been described in terms of one or more preferred embodiments, and it should be appreciated that many equivalents, alternatives, variations, and modifications, aside from those expressly stated, are possible and within the scope of the invention.

What is claimed is:

1. A method for measuring glymphatic flow in a subject using a magnetic resonance imaging (MRI) system, the steps of the method comprising:
   (a) directing the MRI system to acquire data from a subject using a pulse sequence that induces an image contrast in the acquired data that is associated with glymphatic flow;
   (b) reconstructing at least one image from the data acquired in step (a);
   (c) estimating a measure of glymphatic flow from the at least one image reconstructed in step (b); and
   wherein step (a) includes acquiring diffusion-weighted data from the subject using a pulse sequence that includes diffusion-encoding gradients that are designed to have a b-value sufficient to sensitize the diffusion-weighted data to at least one of perfusion of cerebrospinal fluid (CSF) and bulk flow of CSF.

2. The method as recited in claim 1, wherein the b-value is in a range of greater than 0 $s^2/mm$ to about 1000 $s^2/mm$.

3. The method as recited in claim 1, wherein step (a) includes acquiring multiple different diffusion-weighted data sets, each different diffusion-weighted data set being acquired by applying diffusion-encoding gradients along a different diffusion-encoding direction.

4. The method as recited in claim 3, wherein step (c) includes computing a diffusion tensor metric based in part on the multiple different diffusion-weighted data sets, and estimating the measure of glymphatic flow based on the computed diffusion tensor metric.

5. The method as recited in claim 1, wherein step (a) includes acquiring multiple different diffusion-weighted data sets, each different diffusion-weighted data set being acquired using a different b-value.

6. The method as recited in claim 1, wherein the pulse sequence used in step (a) includes applying at least one saturation radio frequency (RF) pulse to saturate spins associated with blood flow before acquiring the diffusion-weighted data.

7. The method as recited in claim 1, wherein step (c) includes computing an apparent diffusion coefficient (ADC) value based in part on the diffusion-weighted data, and estimating the measure of glymphatic flow based on the computed ADC value.

8. The method as recited in claim 1, wherein steps (a)-(c) are performed when the subject is in an awake state to produce an estimate of the measure of glymphatic flow in the subject's awake state, and further comprising repeating steps (a)-(c) when the subject is in a sleep state to produce an estimate of the measure of glymphatic flow in the subject's sleep state.

9. The method as recited in claim 8, further comprising producing a biomarker that indicates at least one of a neurological state or a neurological disease, based in part on the estimate of the measure of glymphatic flow in the subject's awake state and estimate of the measure of glymphatic flow in the subject's sleep state.

10. The method as recited in claim 1, wherein steps (a) and (b) are performed when the subject is in an awake state to reconstruct an image associated with the awake state, steps (a) and (b) are performed when the subject is in a sleep state to reconstruct an image associated with the sleep state, and step (c) includes estimating a relative change in glymphatic flow between the awake state and the sleep state based on the reconstructed images.

* * * * *